United States Patent [19]

Partenheimer

[11] 4,089,807
[45] * May 16, 1978

[54] REACTIVATION OF A PHOSPHORUS-VANADIUM-OXYGEN COMPLEX OXIDATION CATALYST

[75] Inventor: Walter Partenheimer, Naperville, Ill.

[73] Assignee: Standard Oil Company (Indiana), Chicago, Ill.

[*] Notice: The portion of the term of this patent subsequent to Apr. 26, 1994, has been disclaimed.

[21] Appl. No.: 789,536

[22] Filed: Apr. 21, 1977

Related U.S. Application Data

[63] Continuation-in-part of Ser. No. 616,370, Sep. 24, 1975, Pat. No. 4,020,174, and Ser. No. 753,551, Dec. 22, 1976.

[51] Int. Cl.$^2$ .................. B01J 23/92; B01J 27/28; C07D 307/60; C07D 307/89
[52] U.S. Cl. ......................... 252/415; 260/346.4; 260/346.75; 260/524 R; 260/533 R; 260/533 N; 260/546; 260/597 R; 260/604 R

[58] Field of Search ............ 252/415, 413, 414; 260/346.8 A, 346.75, 346.4

[56] References Cited

U.S. PATENT DOCUMENTS 4,020,174  4/1977  Partenheimer .................. 252/415

Primary Examiner—Winston A. Douglas
Assistant Examiner—P. E. Konopka
Attorney, Agent, or Firm—Stephen L. Hensley; Arthur G. Gilkes; William T. McClain

[57] ABSTRACT

The present disclosure relates to a method of reactivation of phosphorus-vanadium-oxygen complex catalysts which are useful in the oxidation of hydrocarbons in particular acylic aliphatics such as alkanes or alkenes to oxidation products including aldehydes, ketones, acids and anhydrides. The present method of reactivation is implemented by passing selected halide containing materials over the catalyst at reactivation conditions to effect formation of a volatile vanadium compound which is removed from the catalyst. This procedure is applicable to reactivation of catalyst which during normal oxidation process become deactivated.

26 Claims, 1 Drawing Figure

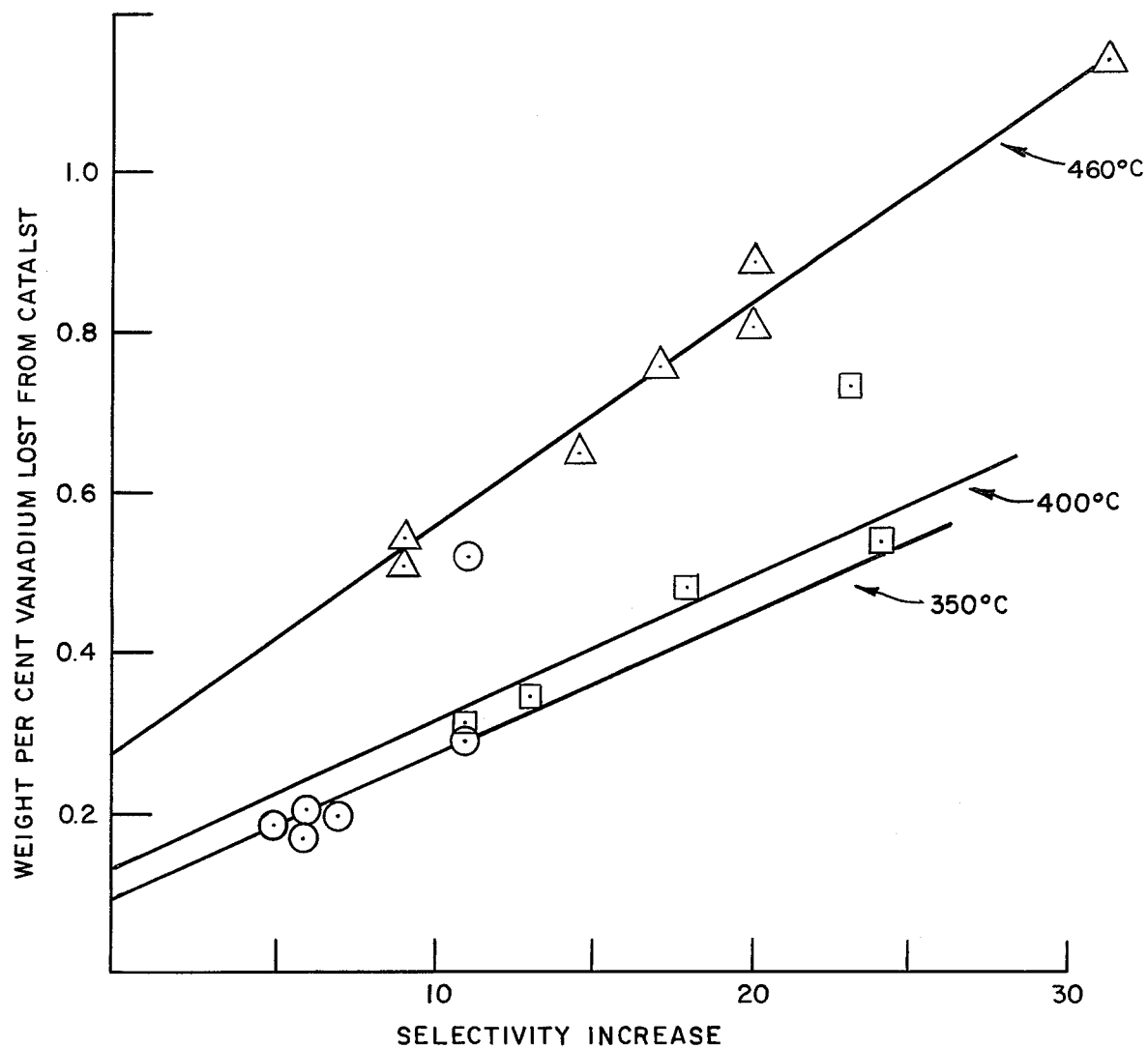

REACTIVATION OF A PHOSPHORUS-VANADIUM-OXYGEN COMPLEX OXIDATION CATALYST

CROSS-REFERENCE TO RELATED APPLICATIONS

This application is a continuation-in-part of my copending applications U.S. Ser. No. 616,370 filed Sept. 24, 1975, now U.S. Pat. No. 4,020,174 and U.S. Ser. No. 753,551 filed Dec. 22, 1976, all the teachings of said applications are incorporated into this application by specific reference thereto.

BACKGROUND OF THE INVENTION

1. Field of the Invention

The field of art to which this invention pertains is reactivation of phosphorus-vanadium-oxygen complex catalysts which are used for the production of oxygenated products including aldehydes, ketones, acids and anhydrides.

2. Description of the Prior Art

During normal processing use of phosphorus-vanadium-oxygen complex catalysts for oxidation of hydrocarbons the catalyst becomes deactivated by many separate reactions including formation of coke and in some cases loss of phosphorus. The former can be treated by well-known methods including controlled burning of the coke. In many prior art processes the loss of phosphorus can be compensated by special treatment of the deactivated catalyst including contacting it with organo-phosphorus compounds as illustrated in U.S. Pat. Nos. 3,296,282 (Cl. 260-346.8) and 3,474,041 (Cl. 252-411). Alkyl phosphates have also been used as taught in West German unexamined application (OLS) 2550119 published May 20, 1976, for reactivation purposes.

Other relevant prior art includes U.S. Pat. No. 2,773,921 issued Dec. 11, 1956, having inventors Paul H. Rylander, Jr. and Wilford J. Zimmerschied. This patent was officially classified in Class 260-683.15 and generally relates to a phosphoric acid-vanadium pentoxide catalyst and a hydrocarbon conversion process using such a catalyst.

Other art which may be pertinent includes the use of chlorides or chlorine in maintaining catalyst activity in reforming or other similar processing. In the case of reforming, chloride addition is utilized to maintain a desired chloride level on the catalyst thereby keeping its acidity high enough for sufficient hydrocracking of paraffins.

SUMMARY OF THE INVENTION

The present invention can be summarized as a process for reactivation of a deactivated phosphorus-vanadium-oxygen complex catalyst by contacting the catalyst with a reactivating agent selected from the group consisting of molecular halogens, and certain compounds containing at least one selected halide.

A broad embodiment of my invention resides in a process for reactivation of a deactivated phosphorus-vanadium-oxygen complex catalyst capable of oxidizing hydrocarbon in the presence of molecular oxygen which comprises contacting said catalyst complex at reactivation conditions with an effective amount of a reactivating agent selected from the group consisting of:

(A) Molecular halogens;

(B) Organic halides being in the vapor state above about 250° C at atmospheric pressure represented by the formula:

$(H)_m C(X)_n$ where each $x$ is a selected halide, $n$ is an integer from 1 to 4 and $m$ is an integer from 0 to 3 consistent with the value of $n$;

(C) Organic halides being in the vapor state above about 250° C at atmospheric pressure represented by the following formula:

$R(X_1)m$ where R is alkane, alkene or alkyne of straight or branched structure having at least two carbon atoms, and $X_1$ is independently a primary, secondary, or tertiary halide, and $m$ is an integer of from 1 to about 20 consistent with the number of carbon atoms of said structures; and (D) Hydrogen halides; or mixtures thereof.

Another embodiment of my invention resides in a process for reactivation of a phosphorus-vanadium-oxygen complex catalyst capable of oxidizing hydrocarbons in the presence of molecular oxygen, which catalyst has been deactivated by a loss of phosphorus during process use which reactivation process comprises contacting said catalyst complex at reactivation conditions with an effective amount of a reactivating agent capable of removing vanadium from said catalyst by formation of a vanadium halide.

DETAILED DESCRIPTION OF THE DRAWING

The attached drawing represents the data generated from the controlled experiment of Example 7 and illustrates one of the benefits from utilizing the claimed invention for reactivation of phosphorous-vanadium-oxygen complex catalysts.

DETAILED DESCRIPTION OF THE INVENTION

The present invention generally relates to a process for reactivation of phosphorus-vanadium-oxygen complex oxidation catalysts by contacting the catalyst with a specified reactivation agent at conditions to effect formation of a volatile vanadium halide.

The claim reactivation procedure accomplishes at least two complimentary results in reactivating phosphorus-vanadium catalysts. First in cases where phosphorus is lost from the catalyst during normal processing the claimed reactivation procedure can help restore the desired atomic ratio of phosphorus to vanadium by causing formation of a volatile vanadium compound which is removed from the catalyst. Second, and of more importance, is the partially selective removal from the catalyst of deactivated catalytic sites on the surface of the catalyst by the claimed reactivation procedure. Many of the deactivated catalytic sites on the catalyst surface comprise vanadium and removal of these sites will improve catalyst performance.

The claimed reactivation agents are selected for their ability to form volatile vanadium compounds which can be removed from the catalyst. In particular the reactivation agents should be selected to allow formation of vanadium halides or vanadium oxyhalides when contacting the phosphorus-vanadium-oxygen complex cataylst. The reactivation agent is generally a halide containing material including molecular halogens, certain organic halides and hydrogen halides.

One of the basic requirements when utilizing the claimed reactivating agents is that they remain in a vapor phase when employed at reactivating conditions and that they form volatile compounds with vanadium. Accordingly then, materials which have reasonably high boiling points are not suitable and would present processing difficulties. It is preferable that the halide materials be in a vapor phase at temperatures above a minimum of about 250° C. at atmospheric pressure. The specific reactivating agents can include pure components or mixtures of components. Specifically utilizable in the reactivating process herein are halides including the gaseous forms of fluorine, chlorine, and bromine. In some instances gaseous iodine may be used but its boiling point is sufficiently high so that it may not present a favorable reactivating agent when used at low temperatures.

Specific reactivating agents can include but are not necessarily limited to the following: chlorine, hydrogen chloride, tetrachloromethane, trichloromethane, dichloromethane, monochloromethane, the halogen substituted ethanes including materials such as ethylene dichloride or other substituted dichlorides and 1-trichloroethane, 1-di, 2-monochloroethane, 1-di, 2-dichloroethane, 1 tri, 2-monochloroethane, 1-tri, 2-dichloroethane, hexachloroethane, tetraboroethylene, halide substituted propanes, butanes (normal or iso), pentanes (normal or branched), hexanes (branched or straight), and other chloride or halide containing aliphatics. Other specific halides which can be utilized include materials such as hexachlorobutadiene, 1,6-dichlorohexane, 1,2-dichlorohexane, 1,2-dibromohexane, 2,2-dichlorohexane, 2,3-dichlorohexane, 2,5-dichlorohexane, and 3,4-dichlorohexane, normal hexylbromide and 3-bromohexane. Iodine, bromine and fluorine can be substituted in many cases into the compounds described above.

Organic halides of fairly low carbon number (generally 4 or less) are generally preferred to reduce the possibility of coke formation during reactivation.

Inter halogens which may be utilized include gases which have reasonably low boiling points such as ClF, ClF$_3$, BrF, BrCl, IBr, BrF$_5$, F$_2$O, Cl$_2$O, ClO$_2$ (potentially explosive), Cl$_2$O$_6$, Cl$_2$O$_7$, Br$_2$O and oxy acids of chlorine, bromine, and iodine. Other materials which may be utilizable at high reactivation temperatures include products such as CF$_4$, CHF$_3$, Freon 12, Freon 13, Freon 22, Freon 21, trichloro acetic acid, thionyl chloride, etc.

The reactivating agents should be non-metal halides. Materials such as PCl$_3$ or PCl$_5$ when passed over the phosphorus-vanadium-oxygen complex catalysts cause phosphorus to be added to the catalyst and do not effect the claimed reactivation procedure.

The reactivation conditions which are contemplated for use in the reactivation process of this invention include the use of an effective amount of a reactivating agent to contact said catalyst and thereby cause at least its selectivity to be increased for the more efficient production of desired oxidation product or products. The reactivating agents which have been described above may either be incorporated into the feed stream passing into the reaction zone or may contact the catalyst in a separate processing procedure. In some instances both operations may be used.

The concentration of the activating agent passing over the catalyst should be monitored so as to prevent damage to the catalyst from excess additions. Additional problems associated with activating agent additions include the production of corrosive end products which possibly could damage plant equipment.

It is also contemplated, whether the reactivating agent is added to the feed passing into the reaction zone or in a separate step, to employ associated processing equipment so as to eliminate passage of noxious products to the environment through the use of suitable scrubbing and/or vapor recovery means.

It has been found in determining what is an effective amount of reactivating agent that there is some minimum concentration of the reactivating agent which should be passed into the reaction zone to effect the increase in selectivity of the catalyst. However, it is difficult to ascertain the concentration as an absolute quantity since reactor designs would have a substantial influence on the actual concentration of regenerating agent contacting the catalyst in the reaction zone. Accordingly then, the better approach would be to state that a minimum total quantity of reactivating agent, based generally on the phosphorus and/or vanadium content in the reaction zone, be passed into the reaction zone for reactivating conditions to give the necessary selectivity increase.

Carrier gases are contemplated when the reactivating procedure occurs as a separate step to move the reactivating agent through the catalyst bed. Such carrier gases can be used as a substitute for the normal feedstock passing into the reaction zone. The carrier gases are not necessarily critical in their choice and can include materials such as nitrogen, butane, oxygen, or any other available gaseous stream which would be compatible with the reactivating agent and would not degrade the catalyst performance.

If a separate reactivation step is used it is contemplated that before or after passage of reactivating agent through the catalyst bed that a gas purge be used to remove entrained reactivating agent and other materials from the catalyst. Such purge materials can include nitrogen or other inert gases or light hydrocarbons such as butane. In many instances after normal oxidation processing it may be required to purge the reactor system with an inert gas or a light hydrocarbon gas to eliminate reaction products or entrained oxygen prior to reactivation as claimed.

Reactivation conditions include temperatures which depend on many factors including whether the reactivating agent is added to the feed in an essentially on-stream operation or whether the reactivating agent is contacted with the catalyst reaction zone in a separate processing step. Of course, when the reactivating agent is present in the feedstock, the temperature of the reaction zone will generally be maintained at that necessary for reasonably efficient and economical production of oxygenation products. When however, the reactivating agent is passed through the catalyst reaction zone in a separate reactivation procedure, large temperature variations may take place.

Specifically the temperature for reactivation should be in the range generally from about 300° to about 650° C. In a preferred instance, the reactivating conditions should include a temperature within the range of from about 300° to about 550° C and in a most preferred instance from about 300° to about 500° C. Of course, the temperature of reactivation will vary depending on the specific catalyst and oxidation process utilized. In a specific instance in which a normal butane feed is passed into the reaction zone for the production of maleic anhydride, it has been found that a preferred reactivating temperature will be somewhere above 300° but below 500° C. when a carbon tetrachloride reactivating agent is used.

For the most successful reactivation of a butane oxidation catalyst for producing maleic anhydride when using a carbon tetrachloride reactivating agent it has been found that reactivation temperatures greater than about 300° C. are needed to cause increases in selectivity but less than about 400° C. are needed to generally prevent excessive losses in catalyst conversion unless a subsequent steam treatment takes place.

The reactivating agents which may be used in the reactivating procedure claimed herein generally include materials such as molecular halogens or mixtures thereof, or compounds containing one or more halide radicals or mixtures thereof. However, within the broad category of halides there possibly could exist materials with hazardous properties such as self-detonation or extremely corrosive materials which while within the definition of halides for reactivating agents would not be effective since they destroy the catalyst and/or the processing equipment. Accordingly then, in defining the halides as used herein, the inoperative species are to be precluded.

In some instances after reactivation of the catalyst using the claimed procedure a steam treatment may be utilized to remove certain impurities laid down on the catalyst during reactivation. Evidence indicates that when using alkyl halides as reactivating agents that at certain temperatures a small amount of carbon residue is laid down on the catalyst adversely affecting its conversion. Accordingly then, it is theorized that the passage of steam over a catalyst in the absence of the reactivating agent will cause a water gas reaction to take place effectively removing the deposited carbon from the catalyst.

The steam treatment may take place by contacting the catalyst with a gaseous stream containing a small quantity of steam. Temperatures can vary and should be sufficiently high to cause removal of the materials deposited on the catalyst during the reactivation procedure. Suggested temperatures are from about 200° to about 500° C.

The vanadium-phosphorus-oxygen catalyst to be reactivated according to this invention comprise vanadium, phosphorus and oxygen combined as a complex. The overall ratio of vanadium to phosphorus in the catalyst bed to be activated will have an atomic ratio in the range of from about ½ to 5 atoms of phosphorus per atom of vanadium. The vanadium-phosphorus-oxygen complex catalyst may also contain various stabilizers and metal additives (generally less than 15 weight percent based on the total weight of vanadium and phosphorus). The atomic ratio of oxygen to the remaining components of the catalyst, when the catalyst is used to catalyze oxidation is difficult to determine and is probably not constant due to the competing reactions of oxidation and reduction taking place during the reduction at high temperatures. The overall ratio of oxygen to the combined atoms of vanadium and phosphorus at room temperature would be such as about 4 to 10 atoms of oxygen per the combined atoms of vanadium and phosphorus.

The vanadium-phosphorus-oxygen catalyst may be prepared in a number of ways. The catalyst may be prepared by precipitating the vanadium and phosphorus compound, either with or without a carrier, from a colloidal dispersion of the ingredients in an inert liquid. The catalyst may also be prepared by dissolving vanadium and phosphorus compounds in a common solvent, such as hot oxalic and thereafter depositing the solution on a carrier. In some instances, the catalyst may be deposited as molten metal compounds on a carrier. The catalyst may also be prepared by heating and mixing anhydrous forms of phosphorus acids with vanadium compounds.

One method for the catalyst preparation is to mix with heating at elevated temperatures anhydrous phosphoric acid such as orthophosphoric acid, pyrophosphoric acid, tripoly or trimeta phosphoric acid, with a vanadium compound such as vanadium pentoxide or ammonium metavanadate. The reaction mixture may be formed on carriers or shaped in the form such as pellets, prior to the reaction to form the catalyst. Another example for the preparation of the catalyst is to dissolve a vanadium compound such as ammonium metavanadate or vanadium pentoxide in an aqueous solution of phosphoric acid. After the components have been dissolved, the solution is heated until precipitation occurs. The precipitant can then be dried and used as a catalyst, or a carrier may be combined with a liquid phase either before or after the precipitation.

In the various methods of preparation of the vanadium-phosphorus-oxygen catalyst, any vanadium and phosphorus compounds may be used as starting materials, which when the compounds are combined and heated to dryness in air at a temperature of, for example, 350° C. will leave as a deposit a catalyst complex having relative proportions within the described ranges. Of course, certain methods of catalyst preparation are preferred. As a source of phosphorus, various phosphorus compounds may be used, such as trimetaphosphoric acid, tripolyphosphoric acid, pyrophosphoric acid, orthophosphoric acid, phosphorus pentoxide, phosphorus oxyiodide, ethyl phosphate, methyl phosphate, amine phosphate, phosphorus pentachloride, phosphorus trichloride, phosphorus oxybromide and the like. Suitable vanadium compounds useful as starting materials are compounds such as vanadium pentoxide, ammonium metavanadate, vanadium trioxide, vanadyl trichloride, vanadium sulfate, vanadium phosphate, vanadium tribromide, vanadium formate, metavanadic acid, pyrovanadic acid, and the like.

An especially preferred catalyst for the production of maleic anhydride using butane feedstocks is described in detail along with methods of production and its process use in U.S. Pat. No. 3,862,146 issued Jan. 21, 1975, having Edward M. Boghosian as its inventor and assigned to Standard Oil Company (Indiana). The above cited patent is hereby incorporated into this specification by specific reference thereto.

The invention of U.S. Pat. No. 3,862,146 described above can be summarized as an oxidation process using a phosphorus-vanadium-oxygen complex metal promoted catalyst for the production of oxygenated products and in particular maleic anhydride.

The above cited patent can be abstracted as follows:
The oxidation of butane to maleic anhydride in the presence of a phosphorus-vanadium-oxygen complex catalyst is enhanced by the addition to the catalyst of a zinc, bismuth, copper or lithium metal activator.

The yield of the oxidation may be increased by as much as 50% without any loss in selectivity to the production of maleic anhydride.

The broadest claim of said referenced U.S. Patent is included below:

A process for the preparation of maleic anhydride which comprises: contacting a feedstock consisting essentially of 50% at least N-butane and a gas-containing molecular oxygen in the vapor phase with a catalyst complex consisting essentially of phosphorus-vanadium-oxygen and a metal activator selected from zinc, copper, bismuth, lithium or mixtures of these, said catalyst complex comprising from about 0.5 to 5 atoms of phosphorus for each atom of vanadium and from 0.05 to 0.5 atoms of said metal activator for each atom of vanadium.

While the above reference patent does specifically describe a certain process and catalyst using such process, the present disclosure is not necessarily limited to all stated limitations of such patent.

Basically the present invention is applicable to catalysts as described in the referenced patent along with the other phosphorus-vanadium-oxygen complex catalysts described above. Such catalysts may also contain additives or stabilizers which may include compounds or metals of zinc, copper, lithium, bismuth or other materials from group IA or IIA of the Periodic Table of the Elements. A particularly good teaching for the production of representative catalysts can be found in U.S. Pat. No. 3,288,731 issued 1966 to R. O. Kerr or U.S. Pat. No. 3,293,268 issued 1966 to R. I. Bergman and N. W. Frisch, the teachings of which are incorporated into the specification by specific reference thereto.

The process of this invention is applicable generally to reactivation catalysts used for the oxidation of hydrocarbons. Such oxidation processes are accomplished by passing a mixture of the desired hydrocarbon and molecular oxygen over the catalyst at reaction conditions to effect the production of the desired products.

The choice of feedstocks, reaction conditions and catalyst will determine the products obtained. Feed materials which can be used include alkanes, alkenes, aromatics which are generally converted to maleic anhydride as the selected oxygenated product. Of the aromatics benzene is generally preferred for maleic anhydride production. Normal butane is the preferred alkane especially in relatively high concentrations. In an especially preferred instance, the feed material should contain over 50 weight percent of its total hydrocarbon content as normal butane. Mixtures of butanes with butene or butadiene may be used for production of maleic anhydride. Ortho-xylene can be used as a feed in which instance the selected oxygenated product is phthalic anhydride. Other feedstocks include propane, propene, pentanes, pentenes or higher aliphatics whether unsaturated or saturated, branched aromatics and cyclo paraffins.

The oxidation of the feed hydrocarbons may be accomplished by contacting low concentrations of hydrocarbon in oxygen in contact with the vanadium-phosphorus-oxygen catalyst. Air is the most economical source of oxygen, but mixtures of oxygen and diluent gases, such as nitrogen, may also be employed. Air streams enriched with oxygen may also be used. The gaseous feed stream to the reactor normally will contain about 0.3 to about 3.0 mol percent hydrocarbons based on the total gaseous stream. About 0.75 to about 2.0 mol percent of the hydrocarbon generally gives optimum yield of product, although higher and lower concentrations may be utilized. In some instances hydrocarbon rich feed streams may be used to form the desired products. Such processing is illustrated in U.S. Pat. No. 3,904,652 having Marshall E. Frank as its inventor. The flow rate of the gaseous stream to the reactor may be varied within fairly wide limits, but a preferred range is at the rate of about 50 to 500 grams of hydrocarbon per liter of catalyst per hour, and generally will be within the range of about 75 to 350 grams of hydrocarbon per liter of catalyst per hour. Residence time of the gas stream will normally be less than about 5 seconds, such as from about 0.01 to less than 2 seconds. The best results have been obtained at residence times of less than 1 second. The flow rates and residence times are calculated at standard conditions of 760 mm. of mercury and at 25° C.

The temperature of reaction for the oxidation of the hydrocarbon may be varied. The temperature of reaction will depend to some extent upon the size of the reactor, the hydrocarbon concentration and the particular vanadium-phosphorus-oxygen catalyst being employed. A suitable temperature of reaction is from about 350° C. to about 575° C., as measured at the maximum temperature in the reactor. Better results have been obtained at temperatures from 375° to 525° C. Even more preferred temperatures are in the range of from about 375° to about 425° C. The pressure on the reactor is not generally critical, and the reaction may be conducted at atmospheric, super-atmospheric, or below atmospheric pressure.

EXAMPLE 1

In this example various feedstocks were passed over a commercial phosphorus-vanadium-oxygen complex catalyst to illustrate some of the oxidation products which could be produced using such a catalyst.

The catalyst was similar in composition to that described in Example I of U.S. Pat. No. 3,862,146 cited above. The reaction conditions were varied to take account of the various feedstock properties and to allow quick screening tests to take place. The hydrocarbon was passed over the catalyst diluted to about one volume percent in air.

The following terms are defined as shown below to help interpret the data:

$$\text{Conversion} = \frac{\text{moles hydrocarbon feed consumed}}{\text{moles hydrocarbon charged}}$$

$$\text{Selectivity} = \frac{\text{moles desired oxidation product produced}}{\text{moles hydrocarbon feed consumed}}$$

Mole Yield = (Conversion) (Selectivity)

In instances in which a weight yield is desired for the production of a certain oxidation product the following calculation can be used.

Weight Yield =

$$(\text{Selectivity}) \frac{(\text{Molecular weight of product})}{(\text{Molecular weight of hydrocarbon feed})}$$

The above conversion, selectivity and yields on the molar basis times 100 equal percentage conversion, selectivity and mole yields. When determining a weight yield it is necessary to know the ratio of the molecular weights of the feed hydrocarbon and the oxygenation product. For example, the weight yield for the production of maleic anhydride from normal butane is defined as the product of the molar conversion times the molar selectivity (for normal butane to maleic anhydride) all times 1.69. The theoretical maximum production of maleic anhydride from normal butane would give a weight yield of 1.69 pounds of maleic anhydride for each pound of normal butane consumed assuming 100 percent selectivity and conversion. In stating the weight yield on a percentage basis, it merely reflects the quantity of weight yield of maleic anhydride times 100. Accordingly then, the theoretical weight percent yield would be 169 percent.

The following results were obtained when oxidizing various feedstocks over the above catalyst.

Methane, when passed over the catalyst at 500° gave three percent conversion, with the majority of products represented as oxides of carbon.

Ethane feed produced similar products as methane above except at 500° C conversion was about 47 percent. Ethylene feed at 500° C resulted in conversions about twice as high as ethane with most of the product material produced as an oxide of carbon.

Propane feed resulted in a molar yield of about 11 percent with the major products being acrylic acid and acetic acid with traces of maleic acid. Propylene feed at 400° C resulted in 95 percent conversion and at 350° C about 38 percent yield of isolated products. Of the products recovered 68 weight percent was maleic acid, 14 weight percent was acetic acid, and 19 weight percent was acrylic acid.

Normal butane feedstock produced maleic acid as the primary product when the effluent from the reaction zone was collected in water. Small quantities of acetic acid and acrylic acid were also produced. Isobutane gave similar products but lower selectivities than that obtained for normal butane.

Pentane feedstock at 400° C produced maleic acid products. Hexane, n-heptane and n-octene feedstocks all produced quantities of maleic acid, acetic acid and acrylic acid.

Paraxylene feedstock produced at 400° C reaction temperature maleic acid, acetic acid, and acrylic acid with some maleic anhydride collected in the non-aqueous collecting traps used.

Orthoxylene at 425°–450° C reaction temperature produced phthalic anhydride and some phthalic acid.

Naphthalene feedstock produced phthalic anhydride.

EXAMPLE 2

In this example a catalyst identical to that described in Example 1 above which had been contacted with a butane and air mixture for a certain period of time was reactivated with a carbon tetrachloride treatment and thereafter put back on stream to show the effects of the halide treatment on the spent catalyst. There was an improvement in yield and selectivity as a result of such a treatment.

The carbon tetrachloride treatment was performed by adding the carbon tetrachloride to the normal butane and air feed mixture. The feed stream contained approximately 1.1 volume percent of normal butane feed in an artificially formulated air atmosphere. The feed stream was passed through a reactor which contained a catalyst as described which had a phosphorus to vanadium atomic ratio of about 1.2 and a zinc metal promoter present in an atomic ratio with respect to vanadium of about 0.2. During normal operations the weight hourly space velocity of the feed containing butane and air was regulated at about 1.4 at atmospheric pressure. The same space velocity and pressure was maintained when carbon tetrachloride additions were made to the feed stream.

During a thirty minute period for carbon tetrachloride treatment the 1.1 volume percent butane feed stream was passed through a scrubber which contained liquid carbon tetrachloride maintained at 0° C. and thereafter into the reaction zone which was maintained at 400° C. temperature. Vapor pressure calculations indicated that the feed passing into the reaction zone contained about 4.1 volume percent concentration of carbon tetrachloride. The carbon tetrachloride treatment as shown in Table 1 below causes a substantial improvement in selectivity of the catalyst for the production of maleic anhydride after about 22 hours operation. Also included in the data shown in Table 1 is the performance of the original fresh catalyst at 420° C. reaction temperature and the temperature of a spent catalyst showing the conversion selectivity and weight yields at 450° C. reactor temperatures prior to the reactivating procedure.

TABLE 1

| Time on Stream, hrs | Reactor Temp., ° C. | Conversion Percent | Selectivity Percent | Weight Yield Percent |
|---|---|---|---|---|
| Original fresh catalyst | 450 | 83 | 62 | 87 |
| Spent catalyst | 450 | 94 | 27 | 43 |
| 18 (CCl$_4$ Treatment) (30 mins.) | 400 | 82 | 50 | 69 |
|  | 450 | — | — | — |
| 40 | 400 | 22 | 76 | 29 |
| 66 | 450 | 79 | 60 | 80 |
| 90 | 450 | 86 | 59 | 86 |
| 186 | 450 | 94 | 52 | 83 |
| 216 | 420 | 97 | 60 | 89 |
| 379 | 420 | 88 | 60 | 89 |
| 499 | 410 | 88 | 59 | 88 |
| 1948 | 400 | 77 | 61 | 80 |

EXAMPLE 3

In this example approximately 10 grams of a spent maleic anhydride catalyst having the same essential composition as that described for the catalyst in Example 2 was placed in a glass-lined tubular oven, blanketed with a flow of nitrogen gas and heated to 400° C. The nitrogen stream was then passed through a solution of concentrated aqueous hydrochloric acid at room temperature. The acid saturated stream was then passed into the tubular oven. Four hours later at 400° C., the hydrogen chloride treatment was terminated and the catalyst was cooled down under a stream of pure nitrogen gas. The catalyst was loaded into a small reactor similar in operation to that described for Example 2 and fed a 1.1 percent normal butane in air feed stream at a weight hourly space velocity of 1.4 at a temperature of 400° C. and atmospheric pressure. Reported results for conversion, selectivity and yields are shown for both the spent catalyst prior to the hydrogen chloride treatment and for the treated catalyst at up to 230 hours of on stream operation.

TABLE 2

| Time on Stream, hrs. | Reactor Temp., °C. | Conversion Percent | Selectivity Percent | Weight Yield Percent |
|---|---|---|---|---|
| Spent Catalyst | 400 | 77 | 56 | 73 |
| 18 | 400 | 73 | 66 | 82 |
| 41 | 400 | 74 | 69 | 86 |
| 185 | 400 | 76 | 69 | 88 |
| 233 | 400 | 76 | 67 | 86 |

EXAMPLE 4

In this example the in-situ addition of hydrogen chloride to an on-stream reaction zone was performed. A beneficial effect on the catalyst was observed. During the on-stream reaction a feed stream containing approximately 1.1 volume percent of normal butane in air was passed over a catalyst which was maintained at a temperature of about 400° C., a pressure at atmospheric and a weight hourly space velocity of about 1.4. At various intervals during the reaction of butane to maleic anhydride, hydrogen chloride was passed in admixture with the feed stream over the catalyst bed. The hydrogen chloride treatment took place by first passing the feed stream at essentially atmospheric pressure through a gas scrubber which contained concentrated aqueous hydrochloric acid at room temperature. The air and butane stream essentially saturated at room temperature with hydrogen chloride was then passed into the reaction zone for periods of time as indicated in Table 3 below. After four successive hydrogen chloride treatments the overall yield and selectivity of the catalyst had been substantially improved. The specific results of such on-stream chloride treatment are shown in Table 3 below.

TABLE 3

| Time on Stream, hrs. | Reactor Temp., °C. | Conversion Percent | Selectivity Percent | Weight Yield Percent |
|---|---|---|---|---|
| 257 | 400 | 77 | 51 | 67 |
| 263 (30 min. HCl) | 400 | — | — | — |
| 281 | 400 | 76 | 54 | 70 |
| 286 (20 min. HCl) | 400 | — | — | — |
| 288 | 400 | 75 | 53 | 66 |
| 305 | 400 | 75 | 56 | 71 |
| 310 (20 min. HCl) | 400 | — | — | — |
| 321 | 400 | 75 | 53 | 67 |
| 329 | 400 | 75 | 58 | 73 |
| 333 (35 min. HCl) | 400 | — | — | — |
| 425 | 400 | 74 | 59 | 74 |

EXAMPLE 5

In this example catalyst similar to that described in Example 2 was used to illustrate the effects of gaseous chlorine treatments on catalytic performance.

During normal processing a 1.1 volume percent n-butane in synthetic air feed was passed through a reactor at atmospheric pressure and a regulated weight hourly space velocity of about 1.4. At certain intervals (17, 45, 179, 212 and 227 hours on stream) the feed was interrupted and a gaseous stream of essentially pure chlorine was passed over the catalyst bed at a 1.4 weight hourly space velocity for periods of time ranging from 1 to 30 minutes. Then the feed was resumed and after a period of time ranging from 3 to 28 hours a gas chromatograph analysis was run on the effluent for purposes of determining the influence of chlorine on the catalyst.

The results of this testing are reported in Table 4 below and indicate chlorine does improve the yield.

TABLE 4

| Time On Stream Hrs. | Reactor Temp., °C. | Conversion Percent | Selectivity Percent | Weight Yield Percent |
|---|---|---|---|---|
| Initial Catalyst | 454 | 99 | 33 | 55 |
| 17 (Cl₂ Treatment, 1 minute) | 450 | — | — | — |
| 28 | 452 | 96 | 39 | 63 |
| 45 (Cl₂ Treatment, 5.5 minutes) | 450 | — | — | — |
| 48 | 454 | 93 | 47 | 74 |
| 179 (Cl₂ Treatment, 18 minutes) | 450 | — | — | — |
| 185 | 448 | 94 | 47 | 74 |
| 212 (Cl₂ Treatment, 10 minutes) | 459 | — | — | — |
| 215 | 448 | 89 | 48 | 73 |
| 227 (Cl₂ Treatment, 30 minutes) | 450 | — | — | — |
| 233 | 447 | 87 | 47 | 70 |
| 257 | 416 | 75 | 61 | 78 |

EXAMPLE 6

In this example carbon tetrachloride reactivations were performed under conditions similar to those described in Example 5 on a catalyst as described in Example 2. Within 4 hours of each carbon tetrachloride activation, the conversion, selectivity and yields were determined. Some of the tests were repeated to illustrate the effects on catalyst performance of multiple carbon tetrachloride activation. In the 330° C. activation test the reaction zone temperature was reduced to 409° from 450° C. in one instance to illustrate the effects of temperature manipulation on catalyst performance.

The data in Table 6 below illustrate: that carbon tetrachloride activations become effective between about 260° and 300° C.; conversion is substantially adversely affected at activation temperatures above 400° C.; and maximum selectivity increases are observed above activation temperature of about 360° C.

TABLE 6

| Test Description | Reactor Temp., °C. | Conversion Percent | Selectivity Percent | Weight Yield Percent |
|---|---|---|---|---|
| 260° C Activation | | | | |
| Base | 450 | 99 | 35 | 58 |
| CCl₄ Activation | 260 | — | — | — |
| Post Activation | 450 | 99 | 35 | 58 |
| 300° C. Activation | | | | |
| Base | 450 | 98 | 34 | 56 |
| CCl₄ Activation | 300 | — | — | — |
| Post Activation | 450 | 97 | 54 | 88 |
| CCl₄ Activation | 300 | — | — | — |
| Post Activation | 450 | 96 | 56 | 91 |
| 330° C. Activation | | | | |
| Base | 450 | 99 | 32 | 53 |
| CCl₄ Activation | 330 | — | — | — |
| Post Activation | 450 | 94 | 52 | 82 |
| Post Activation | 409 | 84 | 64 | 91 |
| CCl₄ Activation | 330 | — | — | — |
| Post Activation | 450 | 95 | 56 | 90 |
| CCl₄ Activation | 330 | — | — | — |
| Post Activation | 450 | 93 | 59 | 93 |
| 356° C Activation | | | | |
| Base | 450 | 97 | 34 | 56 |
| CCl₄ Activation | 356 | — | — | — |
| Post Activation | 450 | 93 | 48 | 75 |

TABLE 6-continued

| Test Description | Reactor Temp., °C. | Conversion Percent | Selectivity Percent | Weight Yield Percent |
|---|---|---|---|---|
| CCl₄ Activation | 356 | — | — | — |
| Post Activation | 450 | 91 | 53 | 82 |
| 400° C. Activation | | | | |
| Base | 450 | 98 | 35 | 58 |
| CCl₄ Activation | 400 | — | — | — |
| Post Activation | 450 | 90 | 63 | 97 |
| 450° C. Activation | | | | |
| Base | 450 | 94 | 33 | 59 |
| CCl₄ Activation | 450 | — | — | — |
| Post Activation | 450 | 50 | 66 | 56 |

EXAMPLE 7

In this example catalyst similar to that used in Example 2 were reactivated at various temperatures using procedures similar to those described in Example 6. The reactivating agent selected was carbon tetrachloride. Vanadium loss from the catalyst was measured after each reactivation and the improvement in catalyst selectivity for production of maleic anhydride from butane was also determined after a period of time subsequent to the reactivating procedure.

The results from this experiment are reported in the drawing and reveal that, for the production of maleic anhydride from butane, a definite relationship exists between the increase in selectivity and the amount of vanadium loss from the catalyst. Furthermore, the temperature of reactivation has an influence on amount of vanadium loss for a given increase in selectivity - lower temperatures being favored. Additionally, the intercepts at the ordinate indicate that some vanadium can be lost from the catalyst without effecting a change in selectivity even though a change in the P/V ratio would occur.

EXAMPLE 8

To further confirm the selective nature of the present reactivation procedure for removal of deactivated sites on the catalyst, reactivation was performed on phosphorus-vanadium-oxygen catalysts similar to those used in Example 2. One catalyst was essentially fresh not having been contacted with a butane-oxygen feedstock for maleic anhydride production. The second catalyst was quite deactivated having previously been in contact with butane and oxygen for production of maleic anhydride.

Contacting each of the catalysts with a carbon tetrachloride reactivating agent at similar operating conditions resulted in a greater vanadium loss from the deactivated catalyst than observed for the fresh catalyst. This observation indicates that the reactivation procedure is selective towards removal of deactivated sites from the catalyst.

I claim as my invention:

1. A process for reactivation of a phosphorus-vanadium-oxygen catalyst capable of oxidizing hydrocarbons in the presence of molecular oxygen, which catalyst has been deactivated by a loss of phosphorus during process use, which reactivation process comprises contacting said catalyst complex at reactivation conditions with an effective amount of a reactivating agent capable of removing vanadium from said catalyst by formation of a volatile vanadium compound, said reactivating agent being in the vapor phase at said reactivation conditions and selected from the group consisting of:

(A) Molecular halogens;
(B) Organic halides being in the vapor state above about 250° C at atmospheric pressure represented by the following formula:

$$(H)_mC(X)_n$$

where each X is a selected halide, $n$ is an integer from 1 to 4 and $m$ is an integer from 0 to 3 consistent with the value of $n$;

(C) Organic halides being in the vapor state above about 250° C at atmospheric pressure represented by the following formula:

$$R(X_1)m$$

where R is alkane, alkene, or alkyne of straight or branched structure having at least two carbon atoms, and $X_1$ is independently a primary, secondary, or tertiary halide, and $m$ is an integer of from 1 to about 20 consistent with the number of carbon atoms of said structure; and (D) Hydrogen halides; or mixtures thereof.

2. The process of claim 1 further characterized in that said catalyst comprises pentavalent phosphorus and tetravalent vanadium.

3. The process of claim 2 further characterized in that said catalyst has an atomic ratio of phosphorus to vanadium in the range of from about 0.5 to about 5.

4. The process of claim 3 further characterized in that said catalyst contains a metal activator selected from the group consisting of lithium, bismuth, zinc, copper or mixtures thereof and having from about 0.05 to about 0.5 atoms of metal activator per atom of vanadium.

5. The process of claim 1 further characterized in that said reactivating agent is a molecular halogen.

6. The process of claim 1 further characterized in that said reactivating agent is an organic halide being in the vapor state above about 250° C at atmospheric pressure represented by the following formula:

$$(H)_mC(X)_n$$

where each X is a selected halide, $n$ is an integer from 1 to 4 and $m$ is an integer from 0 to 3 consistent with the value of $n$.

7. The process of claim 1 further characterized in that said reactivating agent is an organic halide being in the vapor state above about 250° C at atmospheric pressure represented by the following formula:

$$R(X_1)m$$

where R is alkane, alkene, or alkyne of straight or branched structure having at least two carbon atoms, and $X_1$ is independently a primary, secondary, or tertiary halide, and $m$ is an integer of from 1 to about 20 consistent with the number of carbon atoms of said structure.

8. The process of claim 1 further characterized in that said reactivating agent is a hydrogen halide.

9. The process of claim 1 further characterized in that said reactivating agent is selected from the group consisting of Cl₂, HCl, CH₃Cl, CH₂Cl₂, CHCl₃ and CCl₄ or mixtures thereof.

10. The process of claim 1 further characterized in that said reactivating agent is Cl₂.

11. The process of claim 1 further characterized in that said reactivating agent is CCl$_4$.

12. A process for reactivation of a deactivated phosphorus-vanadium-oxygen complex catalyst capable of oxidizing hydrocarbon in the presence of molecular oxygen which comprises contacting said catalyst complex at reactivation conditions with an effective amount of a reactivating agent which is in the vapor phase at reactivation conditions, said reactivating agent being selected from the group consisting of:
(A) Molecular halogens;
(B) Organic halides being in the vapor state above about 250° C at atmospheric pressure represented by the formula:

$$(H)_mC(X)_n$$

where each X is a selected halide, n is an integer from 1 to 4 and m is an integer from 0 to 3 consistent with the value of n;
(C) Organic halides being in the vapor state above about 250° C at atmospheric pressure represented by the following formula:

$$R(X_1)m$$

where R is alkane, alkene, or alkyne of straight or branched structure having at least two carbon atoms, and X$_1$, is independently a primary, secondary, or tertiary halide, and m is an integer of from 1 to about 20 consistent with the number of carbon atoms of said structure; and
(D) Hydrogen halides;
or mixtures thereof, to thereby reactivate said catalyst.

13. The process of claim 12 further characterized in that said reactivating agent comprises molecular halogen.

14. The process of claim 12 further characterized in that said reactivating agent comprises hydrogen halide.

15. The process of claim 12 further characterized in that said catalyst comprises pentavalent phosphorus and tetravalent vanadium.

16. The process of claim 15 further characterized in that said catalyst has an atomic ratio of phosphorus to vanadium in the range of from about 0.5 to about 5.

17. The process of claim 16 further characterized in that said catalyst contains a metal activator selected from the group consisting of lithium, bismuth, zinc, copper or mixtures thereof and having from about 0.05 to about 0.5 atoms of metal activator per atom of vanadium.

18. The process of claim 12 further characterized in that said reactivating agent is an organic halide being in the vapor state above about 250° C at atmospheric pressure represented by the following formula:

$$(H)_mC(X)_n$$

where each X is a selected halide, n is an integer from 1 to 4 and m is an integer from 0 to 3 consistent with the value of n.

19. The process of claim 12 further characterized in that said reactivating agent is an organic halide being in the vapor state above about 250° C. at atmospheric pressure represented by the following formula:

$$R(X_1)m$$

where R is alkane, alkene, or alkyne of straight or branched structure having at least two carbon atoms, and X$_1$ is independently a primary, secondary, or tertiary halide, and m is an integer of from 1 to about 20 consistent with the number of carbon atoms of said structure.

20. The process of claim 12 further characterized in that said reactivating agent is selected from the group consisting of Cl$_2$, HCl, CH$_3$Cl, CH$_2$Cl$_2$, CHCl$_3$ and CCl$_4$ or mixtures thereof.

21. The process of claim 12 further characterized in that said reactivating agent is Cl$_2$.

22. The process of claim 12 further characterized in that said reactivating agent is CCl$_4$.

23. The process of claim 12 further characterized in that said catalyst has an atomic ratio of phosphorus to vanadium in the range of from about 0.5 to about 5.

24. The process of claim 25 further characterized in that said catalyst contains a metal activator selected from the group consisting of lithium, bismuth, zinc, copper or mixtures thereof and having from about 0.05 to about 0.5 atoms of metal activator per atom of vanadium.

25. The process of claim 24 further characterized in that said reactivating agent is selected from the group consisting of Cl$_2$, HCl, CH$_3$Cl$_2$, CHCl$_3$, CCl$_4$, C$_2$H$_5$Cl, C$_2$H$_4$Cl$_2$, C$_2$H$_3$Cl$_3$, C$_2$H$_2$Cl$_4$, C$_2$HCl$_5$, C$_2$Cl$_6$ or mixtures thereof.

26. The process of claim 25 further characterized in that said reactivating agent is selected from the group consisting of Cl$_2$, CH$_3$Cl, CH$_2$Cl$_2$, CHCl$_3$, CCl$_4$ or mixtures thereof.

* * * * *

UNITED STATES PATENT OFFICE
CERTIFICATE OF CORRECTION

Patent No. 4,089,807     Dated May 16, 1978

Inventor(s) Walter Partenheimer

It is certified that error appears in the above-identified patent and that said Letters Patent are hereby corrected as shown below:

Column 16, line 36, Claim 24, "The process of claim 25" should read -- The process of claim 23 --.

Signed and Sealed this

Twenty-sixth Day of December 1978

[SEAL]

Attest:

RUTH C. MASON
*Attesting Officer*

DONALD W. BANNER
*Commissioner of Patents and Trademarks*